United States Patent [19]

Dewald

[11] Patent Number: 4,605,473
[45] Date of Patent: Aug. 12, 1986

[54] HYPOCHLORITE ACTIVATED GOLD ELECTRODE AND MEASURING SYSTEM AND METHOD

[75] Inventor: Lamar R. Dewald, Antioch, Calif.

[73] Assignee: The Dow Chemical Company, Midland, Mich.

[21] Appl. No.: 793,819

[22] Filed: Nov. 1, 1985

[51] Int. Cl.$^4$ .................... G01N 27/30; G01N 27/50
[52] U.S. Cl. .................... 204/1 T; 204/56 R; 204/290 R; 204/400; 204/409; 204/411; 204/412
[58] Field of Search ............... 204/1 B, 400, 409, 411, 204/412, 290 R, 56 R

[56] References Cited

U.S. PATENT DOCUMENTS 3,199,949  8/1965  Clerbois et al. ............... 204/1 T X
4,028,197  6/1977  Capuano ..................... 204/1 T Primary Examiner—G. L. Kaplan
Attorney, Agent, or Firm—James H. Dickerson

[57] ABSTRACT

The present method and apparatus set forth an improved measuring device and system of measuring to determine hypochlorite concentration from electrolyte discharge from a chlor-alkali cell. In the preferred and illustrated embodiment, a container means suspended at the lower end of a wand captures electrolyte. It enables electrodes to be submerged with the electrolyte to obtain a measurement of the hypochlorite concentration. The electrodes include a current emitting electrode, a reference electrode and a gold sensing electrode having an external surface which is etched to increase the surface area and has a coating of hypochlorite thereon to maintain uniform calibration and measurement during operation.

14 Claims, 3 Drawing Figures

U.S. Patent    Aug. 12, 1986    4,605,473
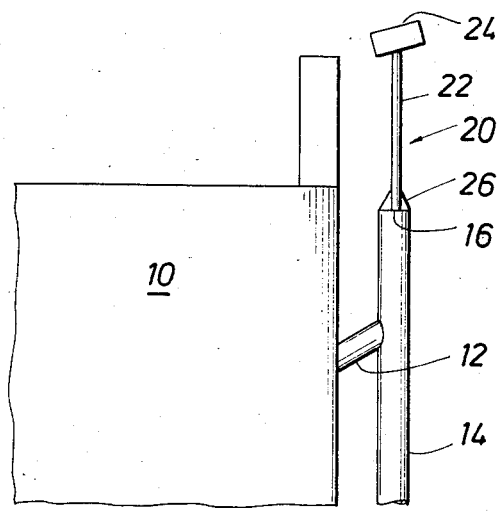
FIG.1
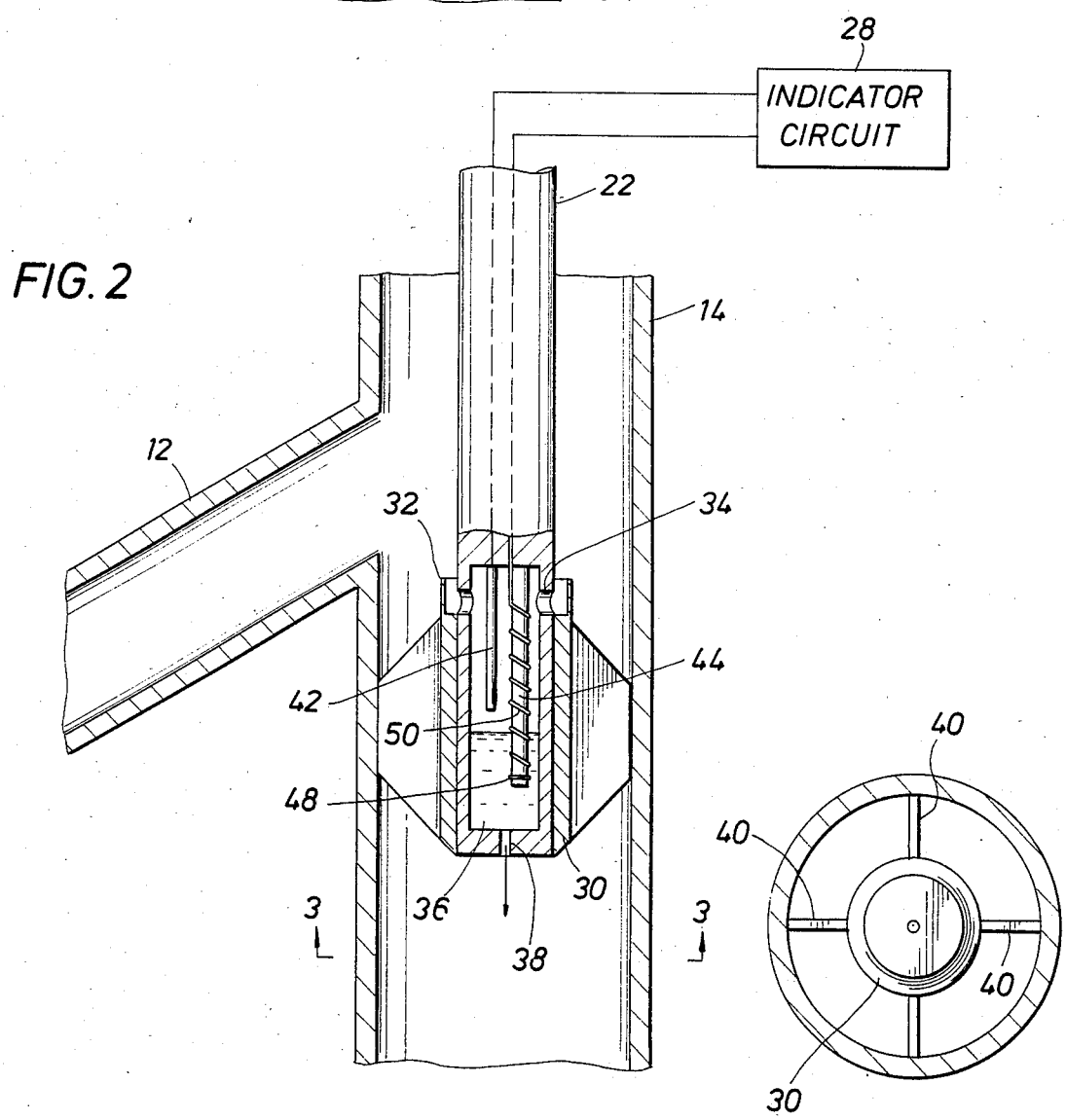
FIG.2
FIG.3

HYPOCHLORITE ACTIVATED GOLD ELECTRODE AND MEASURING SYSTEM AND METHOD

BACKGROUND OF THE DISCLOSURE

In the operation of a chlor-alkali cell sufficiently large to form commercial quantities, cell performance is partially indicated by the presence of hypochlorite. A large, industrial size electrolytic cell provides a continual discharge of electrolyte which flows out of the cell downwardly into a collection pipe for subsequent reuse. The present apparatus is a portable hypochlorite concentration meter particularly incorporating a specially devised gold electrode which measures hypochlorite concentration in the cell discharge or effluent.

Typically, there will be many cells serially connected in a commercial installation. Thus, it is necessary to monitor the performance of each cell often and one procedure for doing this is to test the percent concentration of hypochlorite in the discharge of each cell. A hypochlorite sensitive measuring device, however, encounters certain problems. For one, it is being exposed to chemically active solutions which inevitably attack the measuring device. The attack may take the form of corrosion of measuring electrodes. Another form of difficulty arises in forming a film or coating on the electrodes. When a film is formed, the electrodes have a bias as a result of the film that is formed on them. Moreover, the bias will be irregular; that is, it will change depending on moisture in the film and a number of other factors which are unpredictable. There is another source of irregularity and that relates primarily to drift from the calibration points used in setting up the system. The drift is in part a result of the factors mentioned above. As can be understood, there are many difficulties in obtaining consistent uniform measurements where the measuring instrument itself is not a source of deviation or error.

By contrast, the testing apparatus of this disclosure sets forth a system whereby accurate, repeated measurements can be obtained. Moreover, the device is able to be used often, then stored as typically will occur overnight or through the weekend, and used thereafter without drift or error arising from loss of calibration. The device is intended to be dipped into the discharge electrolyte from electrolytic cells for the purpose of measuring hypochloric concentration. It can thus be used simply by positioning the device in the discharge flow of many electrolytic cells. In fact, it is constructed and arranged so that it is easily positioned to capture the discharge flow so that the hypochlorite concentration is measured in a uniform fashion for serially connected cells. Further, the apparatus enables measurement at a uniform location with respect to the cells so that there is no bias arising from the location at which the electrolyte is measured. In part, this results from the use of an elongate probe having a funnel and cup at the bottom end, the cup capturing the discharge from the electrolytic cell. The cup has a small opening on the bottom to assure that an accumulation of electrolyte is formed in the cup. This assures that the electrodes are submerged. The electrodes are positioned in the cup so that the electrolyte submerges the electrodes.

An important feature is the incorporation of a sensing electrode which is made of gold having an etched surface area to thereby increase the surface area with a coating of hypochlorite thereon. When the device is not in use, it is preferably stored in a aqueous solution of hypochlorite to a specified concentration, thereby renewing the coating. The coating on the device is thus renewed periodically by dipping the device in the solution. This enables the coating of hypochlorite on the electrode to be renewed. This coating assures consistency in operation and thereby enables the device to measure a wide range of hypochlorite concentrations of chlor-alkali cell electrolyte.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is a view showing the measuring apparatus of the present disclosure positioned in a pipe adjacent to a chlor-alkali cell which discharges electrolyte into the pipe to enable measurement of hypochlorite concentration from the cell;

FIG. 2 is an enlarged sectional view through the pipe of FIG. 1 showing details of construction of the measuring apparatus of the present disclosure and in particular means for mounting sensitive electrodes to be submerged in electrolyte from the cell; and FIG. 3 is a bottom view of the apparatus shown in FIG. 2 positioned in the pipe wherein electrolyte is diverted to pass through the measuring apparatus.

DETAILED DESCRIPTION OF THE PREFERRED EMBODIMENT

Attention is first directed to FIG. 1 of the drawings where the numeral 10 identifies a chlor-alkali cell. It forms an electrolyte which is overflowed from the cell through a pipe 12 to flow into a vertical pipe 14. It is removed from the cell for further processing. The pipe 14 is open at the upper end 16. This enables the instrument of the present disclosure identified by the numeral 20 to be positioned in the pipe 14. The measuring instrument 20 includes an elongate probe 22. Indicating apparatus is included in the housing at the top end identified at 24. The position of the probe 22 in the pipe 14 is limited by a set of protruding stops 26 which limit the entry of the probe 22 into the pipe. In other words, the stops 26 serve to register the lower end of the probe at a specified depth in the pipe 14. This will be described in greater detail as it relates to FIG. 2 of the drawings.

The enlarged detail of FIG. 2 shows the pipe 12 which extends to the vertical pipe 14 for discharging a flow of electrolyte. In ordinary circumstances, this flow is continuous. It spills over and falls down the pipe 14 by gravity. The probe 22 is an elongate, hollow wand which encloses certain electrical conductors. The conductors connect with an indicator circuit 28. The conductors extend along the wand up to the indicator circuit 28 which will be described in detail hereinafter. The probe is thus preferably a solid body, or is at least closed by a transverse wall across the bottom portion. The probe terminates by supporting a concentric sleeve 30, the sleeve 30 having an upstanding lip 32 which extends outwardly and upwardly. This lip faces upwardly to capture electrolyte which is funneled into the test area by means of the lip directing the electrolyte flow through ports or openings 34. This introduces the electrolyte into an internal chamber 36. The chamber 36 is drained continuously by a small opening 38. The opening 38 is relatively small so that the rate of drainage is limited. This enables the chamber 36 to be filled substantially during testing. The device is thus positioned below the pipe 12 to capture the discharge. It can be raised in the pipe so that all the electrolyte drains through the opening 38. Thus filling is obtained when the device is positioned as shown in FIG. 2; during retrieval of the probe 22 from the vertical pipe 14, any electrolyte remaining in the chamber 36 is discharged.

The sleeve 30 thus defines the lip 32 which directs the electrolyte to the interior. It also supports a set of alignment tabs 40 which extend radially outwardly. The alignment tabs are sized to fit within the pipe 14 with modest clearance. They are cut back or tapered so that entry is achieved easily. They enable the probe end to slide downwardly in the pipe 14. Recall that the depth penetration is limited by the protruding stop tabs 26 shown in FIG. 1. Axial registration is also controlled in the arrangement shown in FIGS. 2 and 3. This assures that the chamber means 36 is filled with the discharged electrolyte from the chlor-alkali cell 10.

The chamber 36 is the test chamber. In this test chamber, the device includes a thermowell probe 42. A reference electrode is also included at 44. They are physically supported by the probe body thereabove at spaced locations in the chamber 36. A sensing electrode having the form of a gold ring 48 is positioned at the lower end of the reference electrode. It is supported on the structure of the reference electrode. The ring shaped sensing electrode will be discussed in detail below.

The three electrodes as mentioned to this juncture are used in conjunction with a three electrode potentiostat circuit. This known measuring system utilizes a measurement current which is injected into the solution from the thermowell probe 42. The thermowell material is preferably solid platinum or iridium coating on a titanium body to enable current flow into the solution. Further, the thermowell probe operates conventionally to measure solution temperature. It is modified only to the extent necessary to furnish a measurement current flowing into the solution. A standard voltage is established at the reference electrode 44. The sensing electrode 48 is impressed with a fixed voltage versus the reference electrode and the current flow through the sensing electrode 48 is then measured. The current flow from the electrode 48 is proportional to hypochlorite concentration in the chamber 36. A significant factor in this disclosure is the structure of the sensing electrode 48, as more particularly described as an electrode providing reproducibility of data obtained from repetitive use of the measuring device shown in the drawings.

The gold electrode 48 is preferably a solid gold wire wound into a spiral to increase surface area and to mechanically grip the cylindrical surface supporting the wire spiral. The resilient wire coil or spiral of multiple turns resembles a ring having a thickness and diameter described hereafter. It preferably connects with an insulated wire 50. The wire is part of the circuitry which connects with the indicator circuit 28. The gold electrode is formed to a specific size and shape. After construction, it is then etched to increase the surface area of the gold electrode. After etching, the gold electrode is then coated. It is preferably coated with hypochlorite. One suitable procedure for accomplishing this involves the relatively easily accomplished procedure of connecting the gold electrode in a circuit where a small positive voltage (typically about one volt) is impressed on the gold electrode and it is submerged in an aqueous solution of 1.0 m NaCl solution. This can be done for a few minutes, definitely less than one hour. Fifteen minutes is typical and more than adequate. Next, the electrode is positioned for several hours in a solution of $Na_2CO_3$ with an impressed voltage of about $-1.0$ volts applied to the terminal. Thereafter, the electrode is dipped (with the same voltage applied) into an aqueous solution of hypochlorite. A specified concentration is chosen, typically in the range of about 500 ppm; concentrations as high 1000 ppm will also suffice.

When this process is completed, the gold surface has been etched to increase the surface area, and also remove any extraneous films or deposits thereon, and a hypochlorite coating placed on the surface. When the device is in use, it is dipped often into electrolytes which may (or may not) have hypochlorite in them. When the device is not in use it is preferably stored in a container having hypochlorite to a sufficient depth to cover the electrodes. The storage container preferably contains about 250 ppm hypochlorite at a minimum, perhaps as strong as 500 to 800 ppm.

Perhaps some scale should be assigned to certain of the components. The probe 22 length and diameter is really not very important. What is important about the probe construction is that it includes the stops 26 and the alignment fins 40 which position the electrodes just below the pipe 12 to receive the discharged electrolyte to assure that the operative electrodes are submerged in the electrolyte. This enables accurate measurements to be obtained. The electrodes 42 and 44 are typically bought items which can be positioned on mounting blocks which position them spaced from one another so that they can protrude readily into the chamber 36. The finished gold electrode 48 has the form of a small ring like member, perhaps more in the shape of a sleeve having a thickness of perhaps 10 to 20 mils and a width up to about 0.25 in. or 0.6 cm. The diameter is selected to fit snugly around the supporting structure member. If needed, a tab (wire end) is appended so that the conductor connects easily to the gold ring.

Periodically, it may be necessary to renew the etched surface and hypochlorite coating on the gold electrode. When this need arises, the gold electrode is cleaned as might occur on dipping the electrode in a strong acid. The procedure described above is undertaken to renew the hypochlorite coating. This might be done periodically to assure that the device provides repeatable measurements.

In operation, the measuring instrument of this disclosure is used by positioning it in the pipe 14. Positioning is quite easy, being subject to control by the means on the probe or wand which register the electrodes at the desired location to receive the discharged electrolyte for obtaining measurements. Thus, the probe is simply stabbed into the pipe 14 and registered at a specified depth. A few seconds time enables the chamber 36 to fill to overflowing. The indicator circuit 28 performs the measurement of current flow to the electrode 48 and thereby indicates percentage concentration of hypochlorite in some suitable scale. This enables a quick reading to be obtained. This also enables a reading to be obtained which is particularly repeatable from use to use. There is no problem or difficulty arising from repetitive use even though the concentrations of hypochlorite in the individual cells may vary widely from the maximum permitted to zero. Electrode irregularity is thus eliminated and the measurements become far more accurate.

While the foregoing is directed to the preferred embodiment, the scope however is determined by the claims which follow.

What is claimed is:

1. A measuring device for use in measuring hypochlorite concentration from an electrolysis cell forming an electrolyte potentially having hypochlorite therein, the device comprising:
   (a) electrolyte container means having an inlet for admitting electrolyte thereto from an electrolysis cell potentially having hypochlorite therein;
   (b) an elongate probe;
   (c) an exposed reference electrode supported by said probe;
   (d) an exposed gold sensing electrode having a specified surface area, the surface area being etched to increase the surface area thereof;
   (e) a coating of hypochlorite on said sensing electrode surface area;
   (f) circuit means connected to said sensing electrode to measure and indicate hypochlorite concentration of electrolyte from the cell on contacting said electrodes with electrolyte in said container means.

2. The apparatus of claim 1 wherein said container means includes a container having an upwardly facing opening means for receiving downwardly flowing electrolyte from the electrolysis cell, and a drain hole therein for draining electrolyte from said container means.

3. The apparatus of claim 1 wherein said exposed reference electrode is positioned in said container means, said exposed gold sensing electrode is also positioned in said container means, and a current supplying electrode is additionally positioned in said container means wherein all of said electrodes are connected with said circuit means to provide an output indication of hypochlorite concentration.

4. The apparatus of claim 3 wherein the gold electrode is ring shaped and mounted in said container means having an exposed area thereon.

5. The apparatus of claim 4 wherein said ring shaped electrode has a specified thickness, diameter, and height, and wherein the surface area is etched to define a substantially pure gold surface without film or coating thereon.

6. The apparatus of claim 5 wherein the exposed gold surface receives the hypochlorite coating thereon.

7. The structure of claim 6 further including alignment means for positioning said container means at a specified location in a pipe connected to an electrolysis cell for receiving electrolyte therefrom.

8. The apparatus of claim 7 wherein said alignment means includes means positioning said container means at a specified depth in the pipe.

9. The apparatus of claim 7 wherein said alignment means includes means positioning said container means at a specified axial location in the pipe.

10. The apparatus of claim 7 wherein said alignment means includes means positioning said container means at a specified depth and a specified axial location in the pipe.

11. A method of measuring hypochlorite concentration in the electrolyte discharged from the electrolysis cell wherein the electrolyte has varying amounts of hypochlorite therein, the method comprising the steps of:
   (a) positioning container means subject to filling from the discharge of electrolyte from an electrolysis cell;
   (b) positioning a reference electrode in said container means and adapted to be submerged in the electrolyte in said container means;
   (c) positioning an exposed gold sensing electrode in said container means to be submerged by the electrolyte in said container means;
   (d) conducting measurements utilizing said electrodes in the submerged electrolyte to thereby obtain a measurement indicative of hypochlorite concentration;
   (e) and further including the preliminary step of placing a coating of hypochlorite on said sensing electrode.

12. The method of claim 11 wherein the gold electrode is initially coated with hypochlorite after etching the surface thereof.

13. The method of claim 12 further including the step of flowing a current through the electrolyte in said container means to obtain a current flow from the gold electrode.

14. The method of claim 13 including the steps of aligning repetitively in multiple uses the electrodes to measure the electrolyte flowing in discharge pipes, and wherein each use requires aligning.

* * * * *